(12) United States Patent
Swetlik et al.

(10) Patent No.: US 6,567,680 B2
(45) Date of Patent: May 20, 2003

(54) DISPOSABLE ELECTRO-CARDIOGRAM TRANSMITTER DEVICE AND ELECTRODE NODE PLACEMENT FACILITATOR

(75) Inventors: Donald Edward Swetlik, Temecula, CA (US); Bibiano Patao Costello, Simi Valley, CA (US); Michael Carl Dilworth, Thousand Oaks, CA (US); Roy Seizo Carr, Chatsworth, CA (US)

(73) Assignee: Medical Data Electronics, Arleta, CA (US)

( * ) Notice: Subject to any disclaimer, the term of this patent is extended or adjusted under 35 U.S.C. 154(b) by 112 days.

(21) Appl. No.: 09/776,324

(22) Filed: Feb. 2, 2001

(65) Prior Publication Data

US 2002/0107435 A1 Aug. 8, 2002

(51) Int. Cl.[7] .............................................. A61B 5/0408
(52) U.S. Cl. ...................... 600/382; 600/391; 600/392; 600/393; 128/903
(58) Field of Search ................................. 600/382, 386, 600/350–353, 509; 128/903

(56) References Cited

U.S. PATENT DOCUMENTS

| | | | | |
|---|---|---|---|---|
| 3,757,778 A | * | 9/1973 | Graham | 128/902 |
| 4,083,366 A | * | 4/1978 | Gombrich et al. | 600/503 |
| 4,318,412 A | * | 3/1982 | Stanly et al. | 600/508 |
| 4,657,023 A | * | 4/1987 | Kuhn | 600/392 |
| 4,662,378 A | * | 5/1987 | Thomis | 600/382 |
| 4,709,704 A | * | 12/1987 | Lukasiewicz | 600/382 |
| 4,957,109 A | * | 9/1990 | Groeger et al. | 600/391 |
| 5,224,479 A | * | 7/1993 | Sekine | 600/393 |
| 5,313,953 A | | 5/1994 | Yomtov et al. | |
| 5,483,967 A | * | 1/1996 | Ohtake | 128/903 |
| 5,634,468 A | * | 6/1997 | Platt et al. | 128/903 |
| 5,749,365 A | * | 5/1998 | Magill | 128/903 |
| 6,289,238 B1 | * | 9/2001 | Besson et al. | 128/903 |
| 6,341,229 B1 | * | 1/2002 | Akiva | 600/393 |

OTHER PUBLICATIONS

"Physiologic Monitoring Systems, Telemetric; ECG Monitors, Telemetric", Healthcare Product Comparison System; Mar. 1999.

* cited by examiner

*Primary Examiner*—Lee Cohen
(74) *Attorney, Agent, or Firm*—Stetina Brunda Garred & Brucker

(57) ABSTRACT

Disposable electro-cardiogram (ECG) transmitter device and a facilitator for proper placement of electro-cardiogram electrode nodes on a body, such as a human body. The device includes a substrate, integral non-replaceable battery and encapsulated waterproof electronics, and at least one data relay conduit integrally disposed on the substrate and capable of operative contact with a human body. Another embodiment includes a human-shaped or other anatomically shaped substrate and at least one data relay conduit integrally disposed on the human-shaped substrate and capable of operative contact with said human body. In this way, data relay conduits may be more easily and properly placed on the human body by placing the conduits at locations corresponding to their human-shaped substrate locations.

53 Claims, 2 Drawing Sheets

DISPOSABLE ELECTRO-CARDIOGRAM TRANSMITTER DEVICE AND ELECTRODE NODE PLACEMENT FACILITATOR

CROSS-REFERENCE TO RELATED APPLICATIONS (Not Applicable)

STATEMENT RE: FEDERALLY SPONSORED RESEARCH/DEVELOPMENT (Not Applicable)

1. Field of the Invention

The present invention is directed to the field of medical devices. More particularly, the present invention is directed to devices for collecting and transmitting of data corresponding to a patient's bodily functioning.

2. Background of the Invention

The use of electro-cardiogram transmitters is well known in the art. Presently, a number of monitoring procedures use a variety of transmitters to remotely monitor a patient's bodily functioning without the patient being physically connected to an electro-cardiogram machine. These wireless, battery powered transmitters are typically used by hospital patients who need to be monitored by hospital caregivers during post surgery or post procedure. These transmitters are tethered around the patient's neck or shoulder, or secured to an item of clothing worn by the patient generally by a fastening mechanism such as a carry-on belt.

Currently, these transmitters have a number of electrocardiogram electrode nodes that are attached at one end to the patient's body, typically by a biologically compatible adhesive, and connected at their opposite end into a connection port on the transmitter unit. The nodes constantly collect data from the human body in the form of small voltage changes at the attachment points, convert the data into electrical signals and forward them to the transmitter unit for transmission to an electrocardiogram machine for analysis.

Though widely used in the art, these transmitters are not without shortcomings. Currently, all known commercially available transmitters are of the reusable type, utilizing replaceable batteries and replaceable electrodes. The transmitter device is continuously on the patient, typically for three to five days at a time during all wakeful and sleeping hours. One shortcoming of such device is the size, as currently even in its smallest configuration the transmitter unit is about the size of a cigarette box, with most being considerably larger and heavier, thus reducing the level of patient's mobility, and comfort, particularly during sleep. Second, after each use the device can be soiled, sometimes severely and requires careful cleaning prior to reuse. This may considerably increase the chance of the transmission of disease from one patient to another when the device is reused for a different patient. Third, it is not readily apparent from these transmitters as to which part of the body is each electrode node to be connected or to which connection port on the transmitter does each node connect, thus constant supervision by a professional is required in both the initial proper placement of the electrode node on the patient's body and the connection to the correct connection port on the transmitter, and subsequent reconnections should one node become detached. Fourth, because the transmitter system requires the use of costly electrocardiogram machines and reusable transmitters, manufacturers have attempted to use pay-per-use systems to minimize the user's capital budget expenses. These systems have not been adopted by the user market and are largely unsuccessful.

What is needed is a disposable device that is made to be small, lightweight, thin, waterproof and comfortable to wear even during sleep and which would readily guide the user as to proper placement of its electrode nodes on the human body. The disposable device does not require capital expenditures by the user.

It is therefore an object of the present invention to provide a disposable electro-cardiogram transmitter device that does not require the connection of electrode nodes to the transmitter by a user nor the installation of batteries. Non-replaceable, integral batteries give the device a predetermined period of use prior to disposal.

Another object of the present invention is to provide an apparatus and associated method for facilitating proper placement of at least one electro-cardiogram electrode node on a human body.

BRIEF SUMMARY OF THE INVENTION

These and other objects are achieved by the various apparatus and associated method of the present invention.

In a broad aspect, the present invention provides a disposable electro-cardiogram transmitter device. The device includes a substrate with integral electronics and batteries and at least one data relay conduit integrally disposed on the substrate and capable of operative contact with a human body.

In another aspect, the present invention is a method for facilitating proper placement of at least one electro-cardiogram electrode node on a human body. The method includes fastening to the human body a human-shaped or other anatomically shaped substrate having at least one node integrally disposed on the human-shaped substrate at an anatomical location and capable of operative contact with the human body at one end, and positioning the end of the node at a predetermined location on the human body wherein the predetermined location substantially corresponds to the anatomical location on the substrate.

In yet another aspect, the present invention provides an electro-cardiogram transmitter device to facilitate proper placement of at least one electro-cardiogram electrode node on a human body. The device includes a human-shaped or other anatomically shaped substrate and at least one data relay conduit integrally disposed on the human-shaped or other anatomically shaped substrate and capable of operative contact with said human body.

The aforementioned summary descriptions were intended to only provide an overview of the exemplary embodiments of the present invention. A more detailed understanding of these features, and of additional features, objects, and advantages of the present invention will be provided to those skilled in the art from a consideration of the following Detailed Description of the Invention, taken in conjunction with the accompanying Drawings, which will now first be described briefly.

DETAILED DESCRIPTION OF THE INVENTION

The present invention is a disposable electro-cardiogram (ECG) transmitter device and a facilitator for proper placement of electro-cardiogram electrode nodes on a body, such as a human body.

Figure 1:
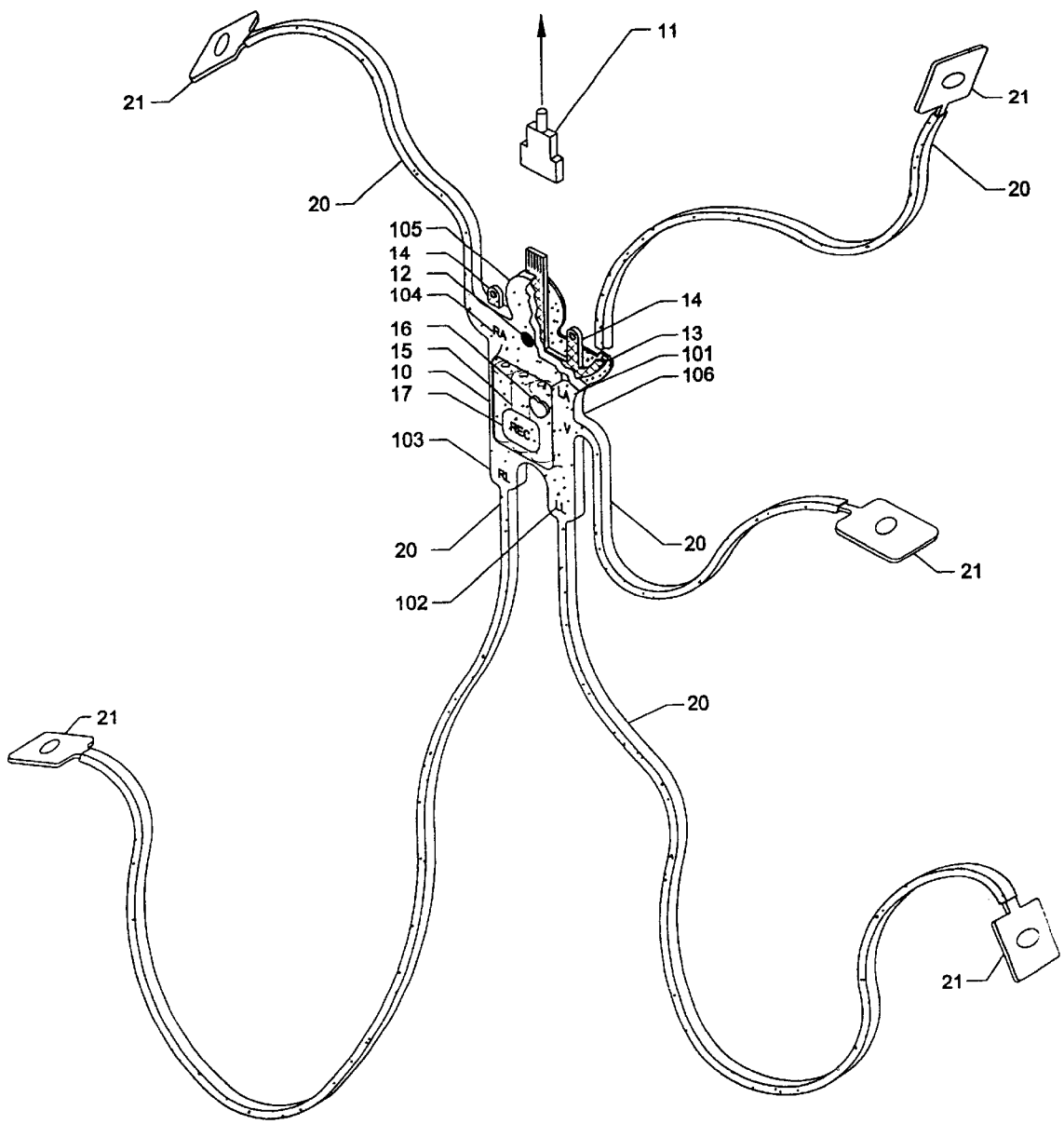
FIG. 1 is a perspective view of an electro-cardiogram transmitter of the present invention illustrating various structural and functional aspects thereof.

As illustrated in FIG. 1, the present invention's disposable ECG transmitter device 1 includes a substrate 10 and at least one of data relay conduits 20, such as an ECG electrode node. Each data relay conduit 20 is integrally disposed on human-shaped or other anatomically shaped substrate 10 and is capable of operative contact with the human body through contact-pad 21 integrally disposed on conduit 20. Each data relay conduit 20 collects and transmits data corresponding to bodily functions of a patient.

By integrally disposing the data relay conduits 20 on the substrate 10, the present invention offers an advantage over the prior art of not using or requiring plug-in connector ports to establish connection between the relay conduits 20 and the substrate 10, thus desirably minimizing the number of components in the device as well as the associated cost, weight and size. In addition, the possibility of erroneous connection of a relay conduit to the device, such connection to a wrong connector port is virtually eliminated.

In an exemplary embodiment of the present invention as shown in FIG. 1, the substrate 10 is shaped in the substantial form of a human or other anatomically shaped body, having the anatomical portions of head 105, left-arm 101, right-arm 104, left-leg 102, and right-leg 103 all integrally disposed on the torso portion 106. Each data relay conduit 20 is in turn integrally disposed on a predetermined location on one of the portions 101–106, such as at the extremity of the legs and arms portions. The predetermined location on substrate 10 corresponds to a substantially proximate corresponding location on the human body at where the contact-pad 21 is to be attached. For example, in the exemplary embodiment shown in FIG. 1, the data relay conduit 20 disposed at the end of left-arm portion 15 signifies that the contact-pad 21 is to be attached to a substantially proximate location on the patient's left arm.

One advantage of the foregoing feature of the present invention is the facilitating of proper placement of the data relay conduits 20, such as an electrocardiogram electrode node or lead wire, on the human body. By being configured to the form of a human or other anatomically shaped body and having the electrode node integrally disposed on the anatomical portions 101–106, the substrate 10 readily provides a user with visual aids as to where to properly connect the contact-pad on the corresponding location on the patient's body. In this way, the need for the presence of, or consultation with a third party for guidance, such as from a professional medical assistant, is vastly reduced thus allowing for proper and expeditious connection of the electro-cardiogram transmitter device 1.

In an exemplary embodiment, each contact-pad 21 has a self-engaging mechanism for engaging the patient's body at desired locations. Examples of self-engaging mechanism include biologically compatible adhesives used alone or in conjunction with a removable protective outer covering that is removed prior to engaging the patient's body.

Referring back to FIG. 1, alternative additional exemplary embodiments of the present invention are also illustrated wherein the ECG transmitter 1 is provided with a securing mechanisms in form of fastener loops 14 or attachment point 13. The fastener loops 14 can be used with a belt or cord that secures the device to the patient or an apparel such as a gown worn by the patient. The attachment point 13 is an adhesive connection having biologically compatible adhesive to secure the ECG transmitter to the body of patient. The fastener 14 and attachment point 13 can each be used alone, or in combination with each other to secure ECG transmitter 1. In addition, in an exemplary embodiment, the substrate 10 is composed of a flexible material so to be configurable in shape to conform to the contours of the human body portion on which it is attached.

The ECG transmitter device 1 can also be provided with an antenna unit (not shown) to transmit data relayed by the data relay conduit to at least one remote receiving source such as an ECG machine. In an exemplary embodiment, the antenna unit is also integrally disposed on one of the data relay conduits 20 to minimize size, cost and weight of the ECG transmitter. In conjunction with the antenna unit, a removable frequency key 11 having one or more predetermined transmission frequencies stored therein can also be used to provide the antenna unit with the desired frequencies to transmit the relayed data. The removable aspect allows for varying of the transmission frequencies by using different frequency keys 11. In addition, the ECG transmitter device 1 can also be provided with at least one communication interface unit such as infrared port 12 to relay one or more predetermined transmission frequencies from a remote source to the device 1 while packaged so that the antenna unit can transmit at one or more of the relayed frequencies. In addition, the ECG transmitter device 1 can be plugged into a programming device at location 105 to achieve a desired transmission frequency.

The ECG transmitter device 1 can also be provided with at least one indicator device such as the light emitting diode (LED) 16 to indicate a patient's heart functioning. In an exemplary embodiment, the LED 16 is heart-shaped to facilitate a user's understanding of its purpose. In addition, the indicator device may also be used in the capacity of indicating the operating condition of the transmitter device 1.

Other exemplary features of the present invention include the expansion port 15 and recording button 17. Expansion port 15 is capable of receiving an external module having operation instruction for device 1, and pressing of recording button 17 effectuates recording of the data at a remote location relayed by the conduits 20. In addition, a power unit such as integral battery 15, is also provided to supply operating power to the ECG transmitter device 1. The power unit may be remotely attached to or integrally disposed on the substrate 10. The ECG transmitter device 1 can also be provided with encapsulated electronics integral to the substrate 10. This would render the device waterproof for use in the shower or bathing.

Figure 2:
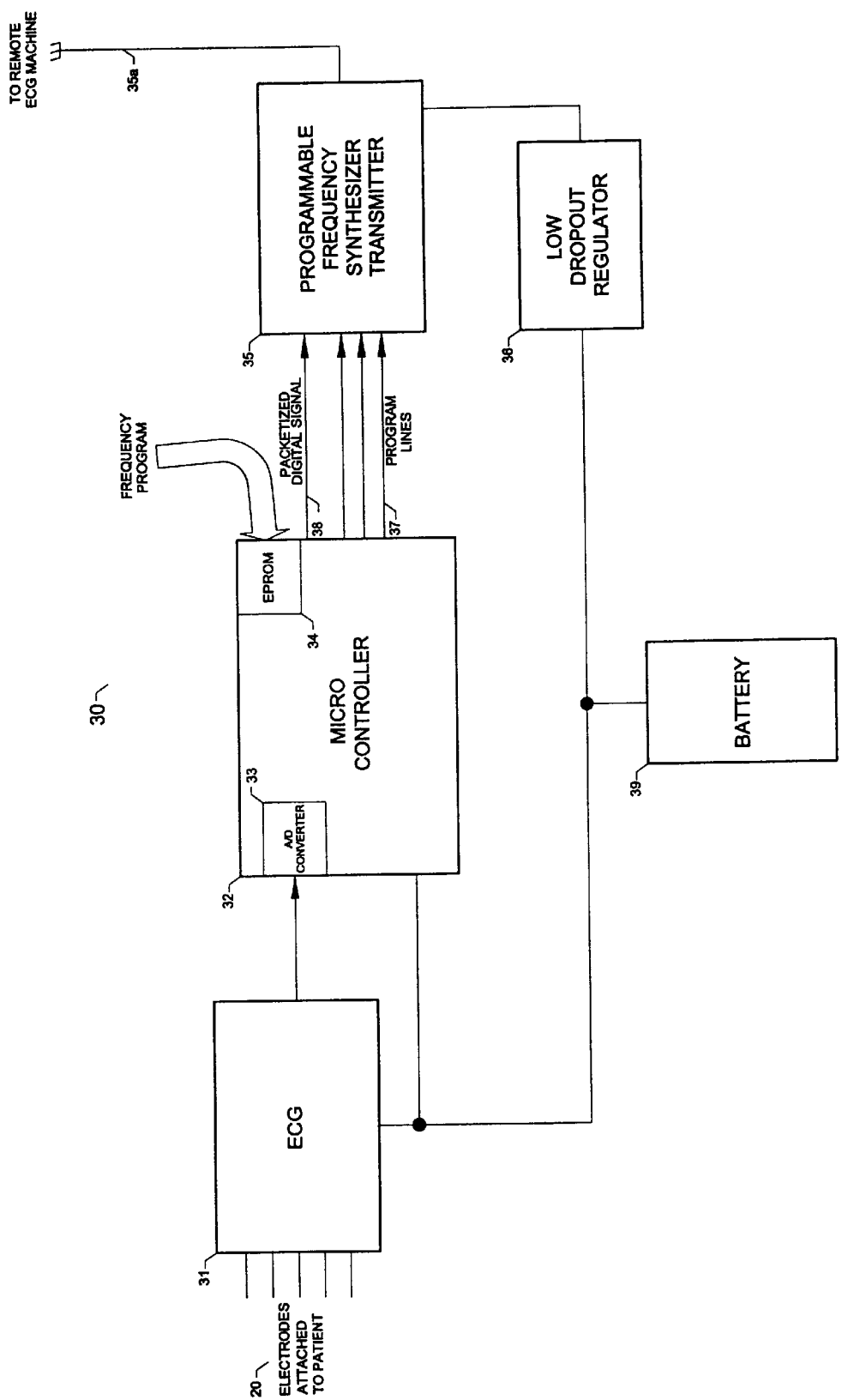
FIG. 2 is a block diagram of the electro-cardiogram transmitter device.

FIG. 2 is a block diagram illustrating the workings of the electro-cardiogram transmitter device. As shown in FIG. 2, data relayed by the conduits 20 are gathered in the electro-cardiograph device 31 and forwarded to the Analog-to-Digital Converter (A/D) 33 in the microcontroller unit 32. The A/D 33 converts the analog data received from the electro-cardiograph device 31 into digital data for processing by the microcontroller unit 32. The microcontroller unit 32 then packets the digitized data signal into a stream of data packets 38 and transmits them via program lines 37 to the programmable frequency synthesized transmitter 35. The programmable frequency synthesized transmitter 35 would in turn transmit the data packets on a predetermined frequency to a remote source 35a, such as an EGG machine for further analysis. The predetermined frequency may be pre-stored on the transmitter 35 or received from the EEPROM unit 34 through the microcontroller 32. The power source unit 39 such as a battery provide power to the CPU microcontroller and to the frequency synthesizer 33 through the dropout regulator.

It should be noted that only the fundamental features of substrate 10 are illustrated in FIG. 1. Those skilled in the art will appreciate that additional surface features, shapes, and details may be provided as desired, including projecting portions, curbs, tabs, buttons, or the like.

Additionally, substrate 10 can be formed of any available biologically compatible light weight material having sufficient flexibility and tensile strength to be made in small sizes and function in its intended environment as a disposable portable ECG transmitter device. Exemplary materials include biologically compatible metals such as stainless-steel and titanium as well as plastics and composites which can include virtually any known or contemplated biologically compatible polymers. In an exemplary embodiment of the disposable electro-cardiogram transmitter, substrate 10 is formed of a flexible plastic material. However, it should be emphasized that this is not a limiting feature of the present invention and that alternative materials may be utilized as appropriate.

Other embodiments, features, and advantages of the present invention will be apparent to those skilled in the art from a consideration of the foregoing specification as well as through practice of the invention and alternative embodiments and methods disclosed herein. Therefore, it should be emphasized that the specification and examples are exemplary only, and that the true scope and spirit of the invention is limited only by the following claims.

What is claimed is:

1. An electro-cardiogram transmitter device to facilitate proper placement of at least one electro-cardiogram electrode node on a human body, said device comprising:
    a human-shaped substrate; and
    at least one data relay conduit integrally disposed on said human-shaped substrate and capable of operative contact with said human body.

2. The device of claim 1, said substrate further comprising:
    a head portion, a left-arm portion, a right-arm portion, a left-leg portion, a right-leg portion and a torso portion wherein said head, left-arm, right-arm, left-leg and right-leg portions are integrally disposed on said torso portion in the substantial shape and configuration of a human body.

3. The device of claim 2, wherein said at least one data relay conduit is integrally disposed on at least one predetermined location on at least one of said portions and wherein said data relay conduit collects and transmits data corresponding to bodily functions of said human body.

4. The device of claim 3 wherein said data relay conduit having at least one contact-pad integrally disposed on said conduit for operative contact with said human body.

5. The device of claim 4 wherein said predetermined location corresponds to a substantially proximate corresponding location on said human body for attachment of said contact pad.

6. The device of claim 5, said contact-pad having a self-adhesive engaging mechanism for engaging said human body.

7. The device of claim 6, wherein said self-adhesive engaging mechanism having a removable protective outer covering wherein said covering is removed prior to engaging said human-body.

8. The device of claim 3, wherein data relay conduit is an electrode lead wire.

9. The device of claim 4 further comprising:
    at least one antenna unit and at least one predetermined transmission frequency, said antenna unit configured for transmission of data relayed by said data relay conduit to at least one remote receiving source at said transmission frequency.

10. The device of claim 9, wherein said remote receiving source is an electro-cardiogram machine.

11. The device of claim 9 further comprising:
    at least one removable frequency selection key having said predetermined transmission frequency stored therein wherein said antenna unit to retrieve said stored frequency and perform said transmission at said frequency.

12. The device of claim 11 wherein said frequency selection key is a programmable frequency selection key.

13. The device of claim 9 wherein said predetermined transmission frequency is determined at the manufacturing time of said device.

14. The device of claim 9 further comprising:
    at least one communication interface unit to relay said predetermined transmission frequency from a remote source to said device wherein said antenna unit to perform said transmission at said frequency.

15. The device of claim 14 wherein said communication interface unit is an infrared communication unit.

16. The device of claim 9 further comprising:
    at least one of an expansion port and recording button disposed on said human-shaped substrate, said expansion port capable of receiving an external module having operation instruction for said device, and said recording button to effectuate recording of said relayed data.

17. The device of claim 4 further comprising:
    at least one non-replaceable, non-rechargeable power unit to supply operating power for a predetermined time to said device wherein said power unit is attached to said substrate.

18. The device of claim 17 wherein said power unit is a battery.

19. The device of claim 4 further comprising:
    at least one remote power unit to supply operating power to said device wherein said power unit is remotely connected to said substrate.

20. The device of claim 4 further comprising:
    at least one indicator device to indicate at least one of a heart beat of said human body and operating condition of said device.

21. The device of claim 20, wherein said indicator device is a light-emitting diode.

22. A method for facilitating proper placement of at least one electro-cardiogram electrode node on a human body, said method comprising:
    fastening to said human body a human-shaped substrate having at least one node integrally disposed on the human-shaped substrate at an anatomical location, said node capable of operative contact with said human body at one end; and
    positioning said end of said node at a predetermined location on said human body wherein said predetermined location substantially corresponds to said anatomical location on said substrate.

23. The method of claim 22 wherein said substrate is substantially flexible.

24. The method of claim 23, said fastening further comprising:

flexing said flexible substrate to substantially conform to a contour of said anatomical location on said human body.

25. The method of claim 22, wherein said node collecting and transmitting data corresponding to bodily functions of said human body.

26. The method of claim 25, wherein said node is an electrode lead wire.

27. A disposable electro-cardiogram transmitter device comprising:

a substrate;

at least one data relay conduit integrally disposed on said substrate and capable of operative contact with a human body; and at least one antenna unit integrally disposed on said data relay conduit and at least one predetermined transmission frequency, said antenna unit configured for transmission of data relayed by said data relay conduit to at least one remote receiving source at said transmission frequency.

28. The device of claim 27, wherein said substrate is substantially flexible.

29. The device of claim 27, wherein said data relay conduit collects and transmits data corresponding to bodily functions of said human body.

30. The device of claim 27, wherein said data relay conduit comprises at least one contact-pad integrally disposed on said conduit for operative contact with said human body.

31. The device of claim 30, said contact-pad having a self-adhesive engaging mechanism for engaging said human body.

32. The device of claim 31, wherein said self-adhesive engaging mechanism having a removable protective outer covering wherein said covering is removed prior to engaging said human-body.

33. The device of claim 27, wherein said data relay conduit is an electrode lead wire.

34. The device of claim 27, wherein said remote receiving source is an electro-cardiogram machine.

35. The device of claim 27, further comprising:

at least one non-replaceable, non-rechargeable power unit to supply operating power to said device wherein said power unit is attached to said substrate.

36. The device of claim 27, further comprising:

at least one remote power unit to supply operating power to said device wherein said power unit is remotely connected to said substrate.

37. The device of claim 35 wherein said power unit is a battery.

38. The device of claim 27, further comprising:

at least one securing mechanism to secure said substrate to at least one of said human body and a clothing gown worn by said human body.

39. The device of claim 38 wherein said securing mechanism is an adhesive connection mechanism.

40. The device of claim 38 wherein said securing mechanism is a fastener mechanism having a fastener loop for securing said device.

41. The device of claim 27, further comprising:

at least one indicator device to indicate at least one of a heart beat of said human body and operating condition of said device.

42. The device of claim 41 wherein said indicator device is a light-emitting diode.

43. The device of claim 27, further comprising:

at least one removable frequency selection key having said predetermined transmission frequency stored therein wherein said antenna unit to retrieve said stored frequency and perform said transmission at said frequency.

44. The device of claim 43 wherein said frequency selection key is a programmable frequency selection key.

45. The device of claim 27, wherein said predetermined transmission frequency is determined at the manufacturing time of said device.

46. The device of claim 27, further comprising:

at least one communication interface unit to relay said predetermined transmission frequency from a remote source to said device wherein said antenna unit to perform said transmission at said frequency.

47. The device of claim 46 wherein said communication interface unit is an infrared communication unit.

48. The device of claim 27, further comprising:

at least one of an expansion port and recording button disposed on said substrate, said expansion port is capable of receiving an external module having operation instruction for said device, and said recording button to effectuate remote recording of said relayed data.

49. The device of claim 27, further comprising:

encapsulated electronics and power source disposed on said substrate for purposes of waterproofing.

50. An electro-cardiogram transmitter device to facilitate proper placement of at least one electro-cardiogram electrode node on a human body, said device comprising:

a human-shaped substrate comprising a head portion, a left-arm portion, a right-arm portion, a left-leg portion, a right-leg portion and a torso portion wherein said head, left-arm, right-arm, left-leg and right-leg portions are integrally disposed on said torso portion in the substantial shape and configuration of a human body;

at least one data relay conduit integrally disposed on said human-shaped substrate and capable of operative contact with said human body, said at least one data relay conduit integrally disposed on at least one predetermined location on at least one of said portions and wherein said data relay conduit collects and transmits data corresponding to bodily functions of said human body, said data relay conduit having at least one contact-pad integrally disposed on said conduit for operative contact with said human body; and at least one antenna unit integrally disposed on said data relay conduit and at least one predetermined transmission frequency, said antenna unit configured for transmission of data relayed by said data relay conduit to at least one remote receiving source at said transmission frequency.

51. An electro-cardiogram transmitter device to facilitate proper placement of at least one electro-cardiogram electrode node on a human body, said device comprising:

a human-shaped substrate comprising a head portion, a left-arm portion, a right-arm portion, a left-leg portion, a right-leg portion and a torso portion wherein said head, left-arm, right-arm, left-leg and right-leg portions are integrally disposed on said torso portion in the substantial shape and configuration of a human body;

at least one data relay conduit integrally disposed on said human-shaped substrate and capable of operative contact with said human body, said at least one data relay conduit integrally disposed on at least one predetermined location on at least one of said portions and wherein said data relay conduit collects and transmits data corresponding to bodily functions of said human body, said data relay conduit having at least one contact-pad integrally disposed on said conduit for operative contact with said human body; and at least one securing mechanism to secure said substrate to at least one of said human body and a clothing gown worn by said human body.

52. The device of claim 51, wherein said securing mechanism is an adhesive connection mechanism.

53. The device of claim 51, wherein said securing mechanism is a fastener mechanism having a fastener loop for securing said device.

* * * * *